United States Patent
Ojima et al.

(10) Patent No.: US 7,829,349 B2
(45) Date of Patent: Nov. 9, 2010

(54) BASE CARRIER FOR DETECTING TARGET SUBSTANCE, ELEMENT FOR DETECTING TARGET SUBSTANCE, METHOD FOR DETECTING TARGET SUBSTANCE USING THE ELEMENT, AND KIT FOR DETECTING TARGET SUBSTANCE

(75) Inventors: Tetsunori Ojima, Kawasaki (JP); Norihiko Utsunomiya, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 672 days.

(21) Appl. No.: 11/738,085

(22) Filed: Apr. 20, 2007

(65) Prior Publication Data

US 2007/0248991 A1 Oct. 25, 2007

(30) Foreign Application Priority Data

Apr. 25, 2006 (JP) .............................. 2006-120682

(51) Int. Cl.
*G01N 33/553* (2006.01)
(52) U.S. Cl. ........................................ 436/525; 436/524
(58) Field of Classification Search ........................ None
See application file for complete search history.

(56) References Cited

U.S. PATENT DOCUMENTS

| 4,444,879 | A | * | 4/1984 | Foster et al. ................ 435/7.95 |
| 5,527,712 | A | * | 6/1996 | Sheehy ........................ 436/525 |
| 5,607,643 | A | | 3/1997 | Xiaoming et al. |
| 5,837,552 | A | * | 11/1998 | Cotton et al. ................ 436/525 |
| 7,195,738 | B2 | | 3/2007 | Utsunomiya |
| 2007/0004019 | A1 | | 1/2007 | Hatakeyama et al. |

FOREIGN PATENT DOCUMENTS

JP 07-146295 A 6/1995

OTHER PUBLICATIONS

C. L. Haynes, et al., "Nanosphere Lithography: A Versatile Nanofabrication Tool for Studies of Size-Dependent Nanoparticle Optics", J. Phys. Chem. B 2001, 105, 5599-5611.
E. Reimhult, et al., "Simultaneous Surface Plasmon Resonance and Quartz Crystal Microbalance with Dissipation Monitoring Measurements of Biomolecular Adsorption Events Involving Structural Transformations and Variations in Coupled Water", Anal. Chem. 2004, 76, 7211-7220.

\* cited by examiner

*Primary Examiner*—Christopher L Chin
(74) *Attorney, Agent, or Firm*—Fitzpatrick, Cella, Harper & Scinto

(57) ABSTRACT

An element to be used for detecting a target substance by using a capturing body for target substance and using surface plasmon resonance has a structure in which the metal structure having a particular pattern is located on a spherical support. Thus configured element for detecting the target substance can detect the target substance at sufficient detection sensitivity in a short period of time by using the surface plasmon resonance. A method for detecting the target substance by using the element and a detection device therefor is provided.

4 Claims, 5 Drawing Sheets

1  2

1  2

1  2

2  3

2  3

2  3

BASE CARRIER FOR DETECTING TARGET SUBSTANCE, ELEMENT FOR DETECTING TARGET SUBSTANCE, METHOD FOR DETECTING TARGET SUBSTANCE USING THE ELEMENT, AND KIT FOR DETECTING TARGET SUBSTANCE

BACKGROUND OF THE INVENTION

1. Field of the Invention

The present invention relates to an element for detecting a target substance, which is useful for detecting the presence or absence of the target substance in a specimen; a base carrier for preparing the same; a detection method with the use of the element; and a kit for detecting the target substance.

2. Description of the Related Art

Conventionally, a measurement method has been known which includes the steps of: preparing a metallic fine particle on which an antibody or an antigen has been previously adsorbed; making the antigen or the antibody cause an antigen-antibody reaction; and observing a change of a spectrum before and after the reaction by using surface plasmon resonance. For instance, Japanese Patent Application Laid-Open No. H07-146295 discloses a method of making a metallic fine particle previously adsorb an antibody corresponding to an antigen of an object to be detected on its surface, and using the metallic fine particle for an antigen analysis. The method includes the steps of: adding the antigen of the object to be measured to the fine particles which have adsorbed the antibody, to cause an antigen-antibody reaction; measuring a Raman spectrum in "a state of a fine particle having an immune complex adsorbed on its surface due to the antigen-antibody reaction"; identifying the formed immune complex; and furthermore, quantifying the added aiming substance on the basis of the intensity of Raman scattered light.

R. P. Van Duyne (J. Phys. Chem. B. 2001, 105, 5599-5611) and F. Hook (Anal. Chem. 2004, 76, 7211-7220) propose a method for improving detection sensitivity in comparison with a method of using a metallic fine particle as an element, by using surface plasmon resonance on an element composed of a thinned film having a nanostructure.

On the other hand, a biosensor to which the present invention is applicable, is a measurement device that makes use of an excellent biomolecule recognition capability of a living body and a biomolecule, and has been expected to be applied to a wide range of not only a medical field but also an environment field or a foodstuffs field, in recent years.

A biosensor generally includes: a capturing body for recognizing and capturing a substance to be measured (hereafter referred to as a target substance); and a detecting element which senses a physical or chemical change occurring after capturing, and converts the change into a detectable signal such as an electrical signal and a light signal. In a living body, there are several combinations of substances having an affinity for each other, such as the combinations of enzyme-substrate, antigen-antibody and DNA-DNA. The biosensor makes use of a principle that one substance of the combination can be selectively measured by immobilizing or carrying the other substance of the combination on a substrate and using the other substance as a capturing component. In addition, various types of detecting elements have been proposed which include an oxygen electrode, a hydrogen peroxide electrode, an ion electrode, ISFET and a thermistor. Recently, even a crystal resonator or an SAW element has been occasionally used, which can sense a change of mass in a nanogram order.

A measuring method using surface plasmon resonance has such characteristics as to merely need a simple structure for an assay because of needing no labeled-molecule such as a fluorescent dye, and be capable of directly monitoring a reaction process in which an object is being adsorbed by a metallic surface, in real time. For this reason, the measuring method using the surface plasmon resonance is expected to be applied to various assays. However, when a conventional element for detecting a target substance with the use of the surface plasmon resonance, such as an element using a fine particle, is used for an affinity assay such as immuno-assay which makes use of the specificity of an antigen-antibody reaction, the element can not occasionally show sufficient detection sensitivity. In addition, an element employing a thin nanostructure formed on a flat substrate can show the sensitivity, but needs a long period of time for a detecting reaction. In other words, a problem of the detection sensitivity and the reaction time is a big subject for expanding an application range of the measuring method using the surface plasmon resonance.

SUMMARY OF THE INVENTION

The present invention is designed with respect to the problems in the above described background art. An object of the present invention is to provide an element which can detect a target substance with sufficient detection sensitivity and in a short reaction time, while using surface plasmon resonance. Another object of the present invention is to provide a base carrier for preparing such an element. Another object of the present invention is to provide a device for detecting a target substance with the use of the detecting element, and a detection method therefor. Another object of the present invention is to provide a detection kit provided with the detecting element and the detection device.

The present invention is directed to a base carrier for detecting a target substance having a support and a metal structure located on the surface of the support, wherein the support is spherical and the metal structure has a maximum size within a range of 10 nm to 1450 nm.

The present invention is directed to an element for detecting a target substance, having a support, a metal structure located on the surface of the support and a capturing body for target substance located on the metal structure, wherein the support is spherical and the metal structure has a maximum size within a range of 10 nm to 1450 nm.

The present invention is directed to a detection method for detecting the presence or absence of a target substance in a specimen or detecting a quantity of the target substance, comprising the steps of: making the element for detecting the target substance contact with a specimen; and detecting a state of the target substance the element.

The present invention is directed to a kit for detecting a target substance, comprising: the element for detecting the target substance, and a device for detecting a target substance in a specimen which is comprised of a unit for making the specimen contact with the element and a unit for detecting a capture of the target substance by the element.

The present invention is directed to a base carrier for detecting a target substance having a support and a metal structure located on the surface of the support, wherein the support is spherical and the metal structure is a thin film having an opening with a maximum opening size of 10 nm to 1450 nm.

The present invention is directed to an element for detecting a target substance, having a support, a metal structure located on the surface of the support and a capturing body for target substance located on the metal structure, wherein the support is spherical and the metal structure is a thin film having an opening with a maximum size of 10 nm to 1450 nm.

The present invention is directed to a detection method for detecting the presence or absence of a target substance in a specimen or detecting a quantity of the target substance, comprising the steps of: making the element for detecting the target substance contact with a specimen; and detecting a capture of the target substance by the element.

The present invention is directed to a kit for detecting a target substance, comprising: the element for detecting the target substance, and a device for detecting a target substance in a specimen which is comprised of a unit for making a specimen contact with the element and a unit for detecting a capture of the target substance by the element.

The above described base carrier can prepare a plurality of metal structures on the above described support so that the respective metal structures can be apart from each other. In this case, the distance between adjacent two metal structures among a plurality of the above described metal structures can be in a range of 50 nm to 2000 nm.

The base carrier can prepare a plurality of the above described openings in the above described metal structure so that the respective openings can be apart from each other. In this case, the distance between adjacent two openings can be in a range of 50 nm to 2000 nm.

The above described base carrier provided by the present invention can include: the above described metal structure; and the above described support. The metal structure can be formed of any one metal of gold, silver, copper and aluminum or an alloy including at least one of them. The support can have a diameter in a range of 0.1 μm to 1000 μm and can be optically transparent. The above optical transparency means that the support passes 70% or higher of visible light therethrough.

An optical detecting unit can be used for the above described detecting unit. The optical detecting unit can include a unit which measures transmitted light, scattered light or reflected light from the above described element. In addition, the optical detecting unit can include a unit that detects a state in which a target substance is captured in the above described element, by using a surface plasmon resonance technique.

The above described detection device can further have a reaction region for making a specimen contact with the above described element, and have a unit for moving the specimen with respect to the above described element.

An optical detection step can be used for the above described detection step. The optical detection step can include a step for measuring transmitted light, scattered light or reflected light from the above described element. In addition, the optical detecting step can include a step for detecting a state in which a target substance is captured in the above described element, by using a surface plasmon resonance technique.

The above described detection step can have a step for moving a specimen with respect to the above described element.

Further features of the present invention will become apparent from the following description of exemplary embodiments with reference to the attached drawings.

Figure 1A:
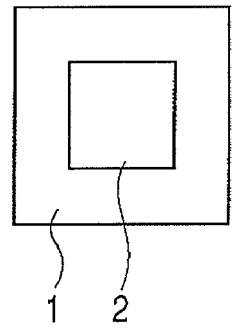
FIGS. 1A, 1B and 1C are views showing various planar shapes of metal structures located on a support.

In the respective drawings, reference numeral 1 denotes a support surface, reference numeral 2 denotes a metallic thin film, reference numeral 3 denotes an opening of a metal structure, reference numeral 4 denotes a resist for electron beam, reference numeral 5 denotes a metal structure, reference numeral 6 denotes an antibody, reference numeral 7 denotes a target substance, reference numeral 8 denotes an element, reference numeral 9 denotes a reaction well, reference numeral 10 denotes a light source unit, reference numeral 11 denotes a spectrophotometer, reference numeral 12 denotes a dispensing unit, reference numeral 13 denotes a specimen reservoir, reference numeral 15 denotes a CPU, reference numeral 16 denotes a display unit and reference numeral 17 denotes an input unit.

DESCRIPTION OF THE EMBODIMENTS

In the next place, each embodiment included in the present invention will be described in detail.

(Base Carrier Structure)

A base carrier for detecting a target substance according to the present invention has a metal structure on a spherical supporting substrate. The metal structure has a particular shape (pattern) on an approximately planar surface on the spherical supporting substrate to improve detecting sensitivity. The metal structure can be formed of a metallic thin film with a film thickness of about 10 nm to about 100 nm.

Figure 1B:
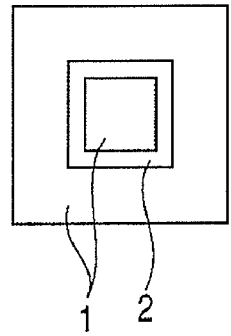
Figure 1C:
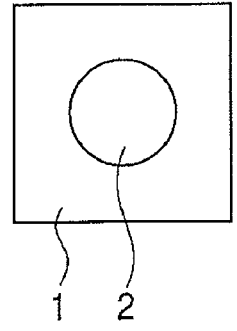

FIGS. 1A to 1C and FIGS. 2A to 2C show examples of a pattern of a metal structure on an approximately planar surface of a spherical supporting substrate. FIGS. 1A to 1C show the examples in which the metal structure formed of a metallic film 2 exists on one part of the surface of the spherical supporting substrate 1. The metal structure can have a pattern including a polygon such as a square shown in FIG. 1A. The metal structure may also have a ring shape as shown in FIG. 1B, a circular shape as shown in FIG. 1C, or an elliptic shape (not shown). The ring shape in FIG. 1B may be the ring based on a polygon such as a square shown in the drawing, or may also be based on the circular shape or the elliptic shape. A plurality of the metallic films 2 may exist at spacings on the surface of the spherical supporting substrate 1.

Figure 2A:
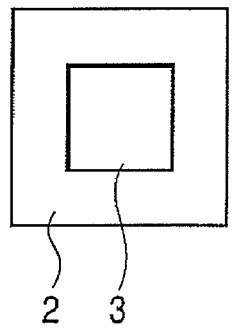
FIGS. 2A, 2B and 2C are views showing various planar shapes of metal structures located on a support.
Figure 2B:
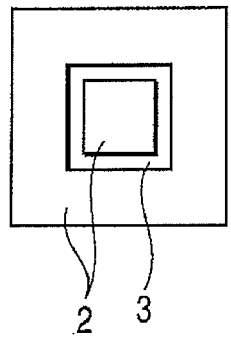
Figure 2C:
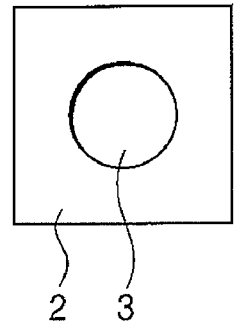

A metal structure may have a pattern as shown in FIGS. 2A to 2C, which has an opening 3 formed in each metallic film 2 having respective shapes in FIGS. 1A to 1C. Specifically, the pattern can include the one having the polygonal opening in the metallic film as shown in FIG. 2A. Alternatively, the pattern may be the one having a ring shape (which has the metal structure again in the opening) as shown in FIG. 2B, or may be the one having a circular or elliptic opening as shown in FIG. 2C. The pattern as shown in FIGS. 2A to 2C may be formed by the steps of forming the metallic film 2 on the whole surface of the spherical supporting substrate 1, and forming the opening 3 in the one part; or by the steps of preparing a plurality of the metallic films 2 which exist apart from each other, and forming the opening 3 in each of them.

A material to be used for forming a metal structure can be any one metal of gold, silver, copper and aluminum, or an alloy containing any one of them. The metal structure on a base carrier may be formed on a thin film of chromium or titanium which has been formed previously on a support, so as to improve the adhesiveness of the metal structure to the support.

Figure 3:
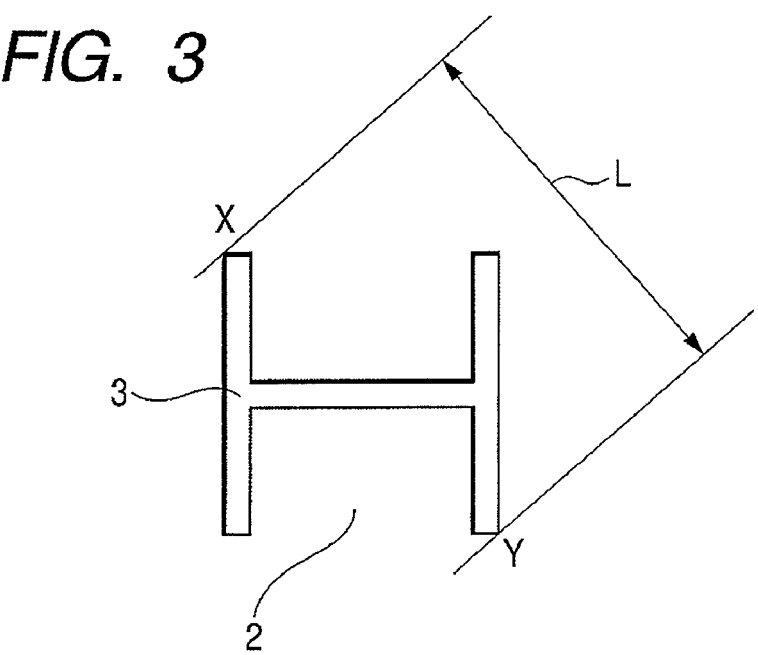
FIG. 3 is a view showing a method for measuring the size of a metal structure.

A pattern of the metal structure has a size, or equivalently, a distance from arbitrary one point to another point on a contour, preferably in a range of 10 nm to 1450 nm. In the above case, the maximum distance between the arbitrary two points should be in the above range. For instance, in the case of the H-shaped pattern as shown in FIG. 3, the distance (L) between the points X and Y shall be within the above described range, because of being maximal. Similarly, in the case of a rectangular ring pattern, the distance along the diagonal line L between points X and Y on the outer perimeter shall be within the above described range, because of being maximal. In the circular shape shown in FIG. 1C or FIG. 2C, the diameter of the outer circumference shall be within the above described range. When having the size of the planar shape in the range, the metal structure can further increase an effect of surface plasmon resonance and provide aiming detection sensitivity.

One or more patterns of metal structures are located on a support as needed. When two or more patterns of metal structures are located, the distance between the respective metal structures can be set at a range of 50 nm to 2000 nm. This is because the plasmon in the metal structure affects to each other and consequently affects the distribution and intensity of a spatial electric field. When the distance is large, the existence density of the metal structure decreases, and the signal intensity may also decrease. In such a case, it is necessary to use a specific optical system. Accordingly, the distance is preferably in the above described range.

The pattern of the metal structure can be located so that the same pattern is regularly arrayed on one support. An element using thus configured base carrier can more easily measure transmitted light, scattered light and reflected light.

A support for forming a metal structure thereon can employ an optically transparent material including glass, quartz, or a resin such as polycarbonate and polystyrene. In other words, it is preferable to use the optically transparent support, particularly when detecting a substance by using a plasmon resonance technique. The support is spherical, but a cross section passing through the center does not always need to be a perfect circle. The diameter of the spherical support is not particularly limited, and can be selected from a range in which a metal structure can be formed on the spherical support and an element can detect a desired target substance, while considering the structure of a detection system.

Figure 4A:
FIGS. 4A, 4B, 4C, 4D, 4E and 4F are views showing steps of forming a metal structure on a support.
Figure 4B:
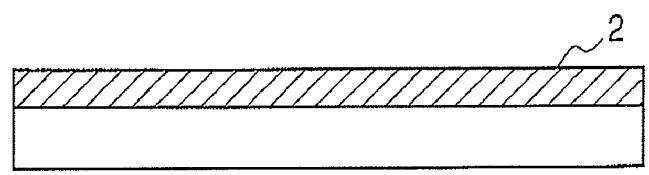
Figure 4C:
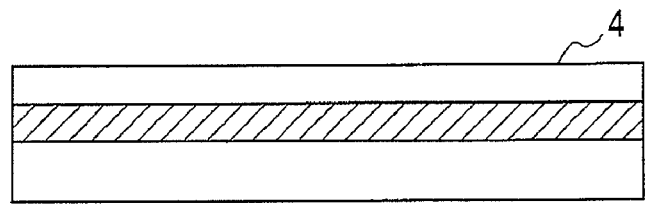
Figure 4D:
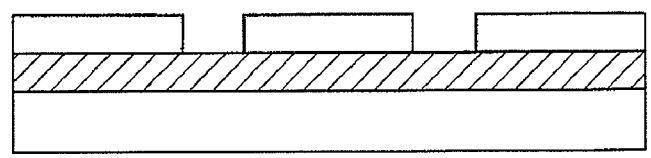
Figure 4E:
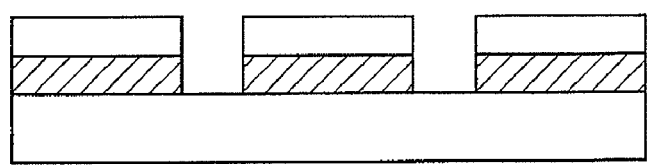
Figure 4F:
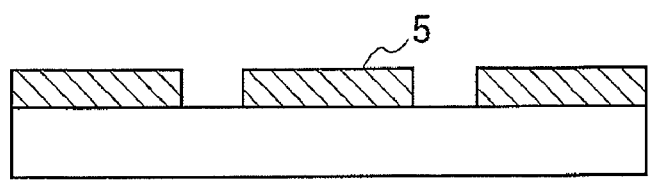

An element for detecting a target substance according to the present invention can be obtained by preparing a base carrier having a metal structure formed on a support and further locating a capturing body on the metal structure of the base carrier. FIGS. 4A to 4F show an example of the preparation method. FIGS. 4A to 4F express the surface of the spherical support with a planar surface for the sake of convenience. As shown in FIGS. 4A to 4F, the support 1 is prepared (FIG. 4A) at first. A metallic film 2 is formed on the support 1 with a sputtering method or a vapor deposition method (FIG. 4B). A resist 3 for an electron beam is layered thereon (FIG. 4C), is exposed to light by an electron-beam lithographic apparatus, and is developed to form a resist pattern (FIG. 4D). Then, an unnecessary metallic film is etched (FIG. 4E), and the resist is removed. The metal structure 5 located in an array form is thus formed (FIG. 4F). The metal structure 5 can be prepared by patterning the resist with a focused ion-beam processing apparatus, an X-ray exposure equipment and an EUV exposure equipment other than the electron-beam lithographic apparatus. More specifically, a colloidal lithography method can be employed which includes, for instance, the steps of: locating fine particles on the support, growing a metallic film in the spaces among the particles, and removing the fine particles.

Figure 5:
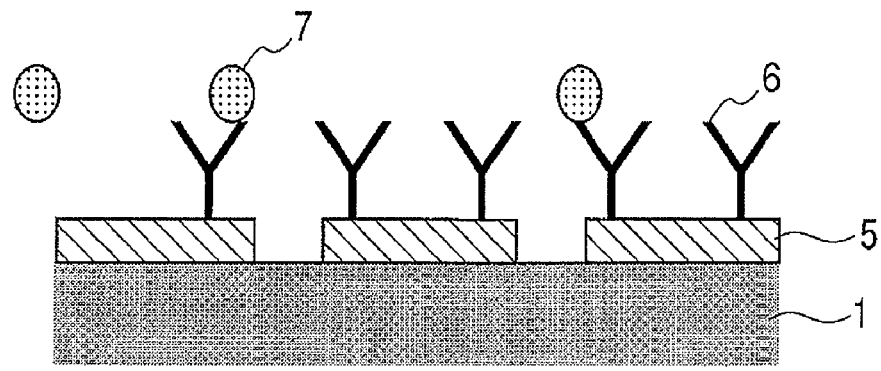
FIG. 5 shows a view for illustrating a structure of an element for capturing a target substance.

The capability of capturing a target substance can be imparted to an element by immobilizing a capturing body such as an antibody 6 on a metal structure 5, as is shown in FIG. 5. When a target substance 7 approaches to the metal structure 5 having the antibody 6 immobilized thereon, a complex is specifically formed on the metal structure, and changes a dielectric constant (refractive index) of the surface of a base carrier. Another example of such a combination as to form the complex includes a complex of an enzyme and a substrate, and such a complementary base pair as to cause the hybridization of DNA, in addition to the combination of antibody-antigen. Either of the respective complexes can be used as a capturing body for the other. The capturing bodies can be immobilized on the surface of the detecting element with a physical or chemical method. The surface of the element can be coated with skim milk, casein, bovine serum albumin, phospholipid, polyethylene glycol, or a derivative thereof, in order to prevent an element from sending a signal originating in so-called nonspecifically adsorbed contaminants.

(Detection Device and Detection Method)

In the next place, a device for detecting a target substance will be described, which employs an element having the above described structure. The detection device according to the present invention includes: at least a unit for making a specimen contact with the element for detecting the target substance; and a unit for detecting a signal sent from the element.

The detecting unit can have: an optical detection system including a light source, a spectroscope and an lens; a reaction well for forming a reaction region for making a specimen moved to the vicinity of an element react with the element therein, and a liquid supply system including a liquid supply mechanism. A usable light source can cover a wavelength range from a visible range to a near-infrared range. For optical measurement, any of an absorption spectrum, a transmission spectrum, a scattered spectrum and a reflection spectrum can be used. The most preferable measuring method is to use a peak wavelength in an absorption spectrum or absorption intensity at a peak. When a target substance is specifically combined with a capturing body prepared on a metal structure provided on the element, surface plasmon resonance changes from an uncombined state. Specifically, the peak wavelength in the absorption spectrum shifts to a longer wavelength side, and the absorption intensity increases. The target substance can be quantified by a degree of a shifted quantity, on the basis of a calibration curve previously prepared for the target substance. The element detects the target substance by using localized plasmon resonance, so that an electric field locally increases in the vicinity of the metal structure. The phenomenon can be detected by surface enhanced Raman spectroscopy (SERS) or surface plasmon fluorescence spectroscopy (SPFS), so that the element according to the present invention can be applied to a measuring method of capturing the target substance and detecting it with these techniques. The method using the techniques also can quantify the target substance.

Figure 6:
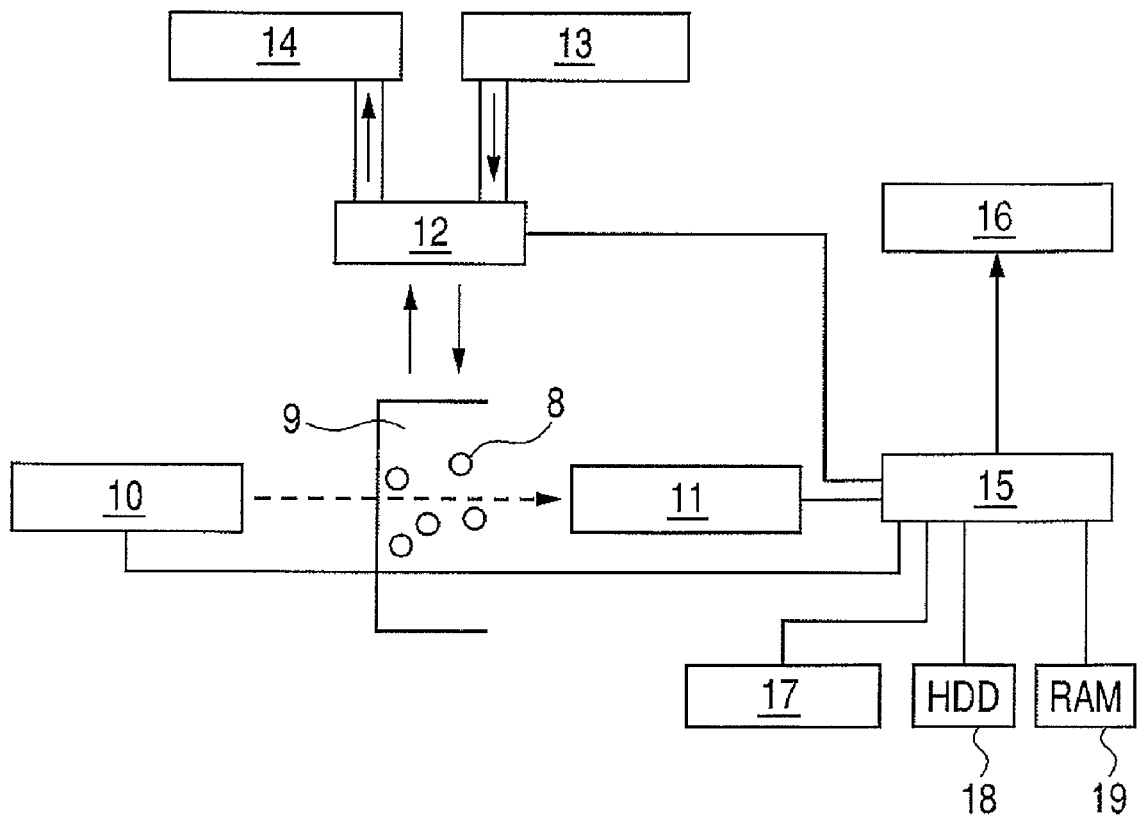
FIG. 6 is a view showing an example of a structure of a device for detecting a target substance.

Next, a representative structure of the device is shown in FIG. 6. First, a reaction well 9 of a reaction region in which a specimen reacts with an element 8 is located between a light source unit 10 and a spectrophotometer 11. The element 8 is previously put in the reaction well 9. On the other hand, a specimen reservoir 13 and a waste fluid reservoir 14 are connected to a dispensing unit 12. The specimen which has been put in the specimen reservoir 13 is transferred to the reaction well 9 by the dispensing unit 12. Then, the target substance reacts with the element 8 while the reaction well 9 is stirred. At this time, the light source unit 10 emits light to make the light pass through the reaction well 9. The spectrophotometer 11 measures a transmission spectrum of the light. A central processing unit 15 compares the transmission spectrum with a previously prepared data for calibration, determines the concentration and the like, and displays the measurement result on a display unit 16. It is acceptable to introduce a phosphate buffer into the reaction well 9 as a cleaning liquid from the dispensing unit 12 and clean the reaction well 9 before measurement, as needed. Here, a change of a spectrum can be measured not only with a static method after a fixed period of time, but also with a dynamic method in real time. In the case, a changing rate with time can be obtained as additional information. The above described operation is input by an input unit 17, a program previously recorded in HDD 18 is loaded into RAM 19, and the operation is carried out.

A kit for detecting a target substance can include the above described element for detecting the target substance and the detection device.

EXAMPLE

In the next place, the present invention will be described in more detail with reference to Example. However, the present invention is not limited to only the following example.

Example 1

Figure 7:
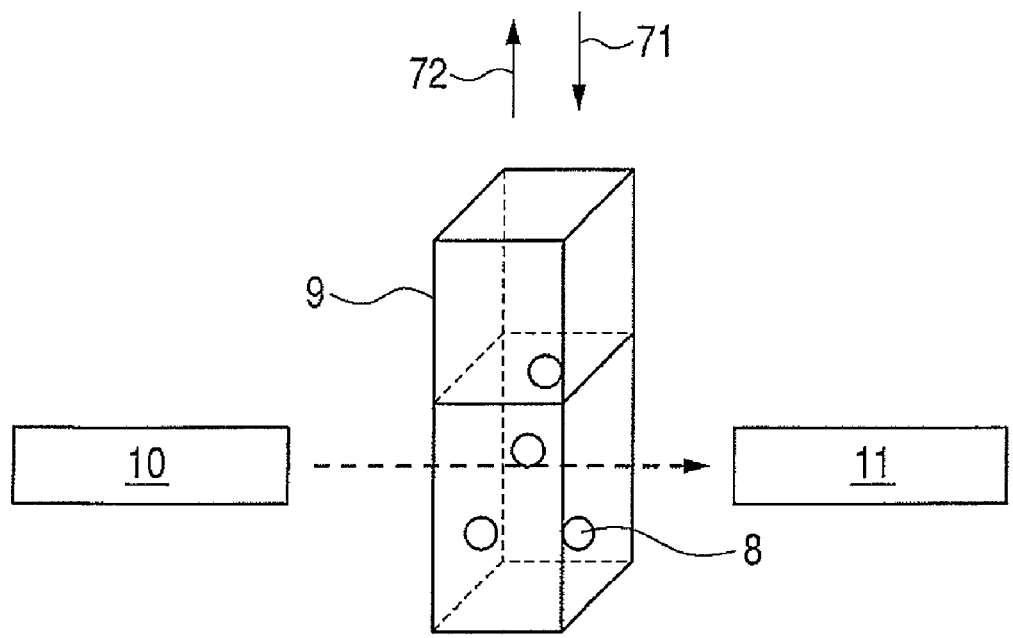
FIG. 7 shows a view for illustrating a structure of a device for detecting a target substance used in Example.
Figure 8:
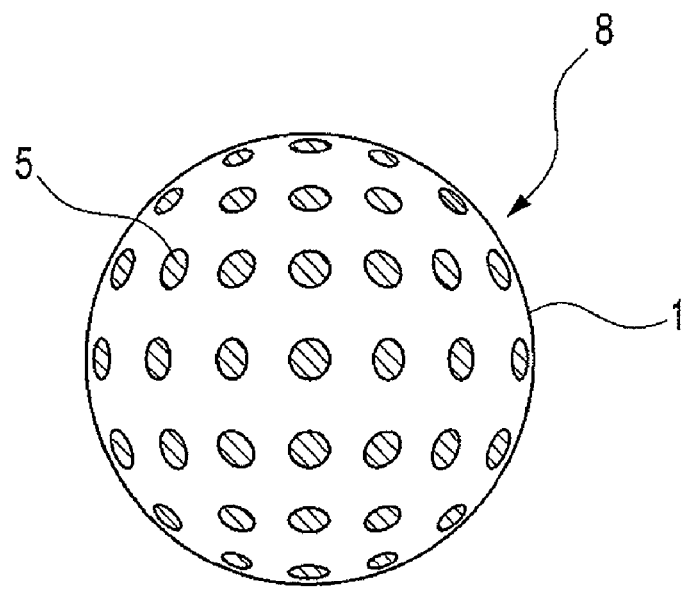
FIG. 8 shows an enlarged schematic block diagram of the detecting element 8 shown in FIG. 7.

FIG. 7 shows a diagrammatic structure of a detection device used in the present example. A detecting element 8 shown in an enlarged duplex view in FIG. 8 is prepared by a technique described below.

At first, a base carrier is prepared by the steps of: forming a gold thin film with a thickness of 20 nm on a quartz bead with a diameter of 100 µm; and forming a predetermined pattern by patterning the gold thin film with the use of an electron-beam lithographic apparatus. The pattern of a metal structure is a square shape of 160 nm×160 nm. The respective patterns are located into an array form at 250 nm spacing.

Next, an immobilization method will be shown which includes immobilizing an anti-AFP (α-fetoprotein) antibody that is a capturing body for target substance to be used in the present example, on the surface of a gold structure, so that the surface of a metal structure can acquire capturing capability. The prepared element is immersed in an ethanol solution of 11-mercaptoundecanoic acid that has a thiol group having a high affinity for gold which is a material for the structure in the present example. Then, the surface of the above described structure is modified. Thereby, a carboxyl group is exposed at the structure surface. The element of the state is similarly immersed in an aqueous solution of N-hydroxysulfosuccinimide (Dojindo Laboratories Corporation) and an aqueous solution of 1-ethyl-3-[3-dimethylamino]propyl]carbodiimide hydrochloride (Dojindo Laboratories Corporation). Thereby, a succinimido group is exposed at the structure surface. Furthermore, the structure surface is modified with streptavidin by combining the succinimido group with streptavidin. A biotinylated anti-AFP antibody is immobilized on the structure.

A detecting element 8 is obtained by the above described steps.

In addition, such a structure as to detect different target substances in a specimen in the same reaction well can be prepared by preparing a plurality of detecting elements and immobilizing respective different antibodies on the respective elements. The respective different antibodies can be immobilized on the respective elements with similar steps to the above described steps.

The concentration of AFP in a specimen can be specifically measured by operating a device in FIG. 7 in the following steps:

(1) introducing a specimen containing AFP which is a target substance, into a reaction well 9 having an element 8 located therein, and making the AFP captured on a metal structure of the element 8 in the reaction well 9;

(2) discharging the specimen from the reaction well 9, and introducing a phosphate buffer into the reaction well 9 as is indicated by an arrow 71 to clean the inside of the reaction well 9; or precipitating the element 8 with the use of a centrifuge and discharging only the supernatant liquid, when discharging the specimen and then cleaning the inside of the reaction well 9; or alternatively, discharging a solution except the element 8 with the use of a filter, introducing a cleaning liquid and then discharging the cleaning liquid again except the element 8 with the use of the filter, as is indicated by the arrow 72; and (3) finally, charging the phosphate buffer into the cleaned reaction well 9 and measuring an absorption spectrum of a gold structure.

Figure 9:
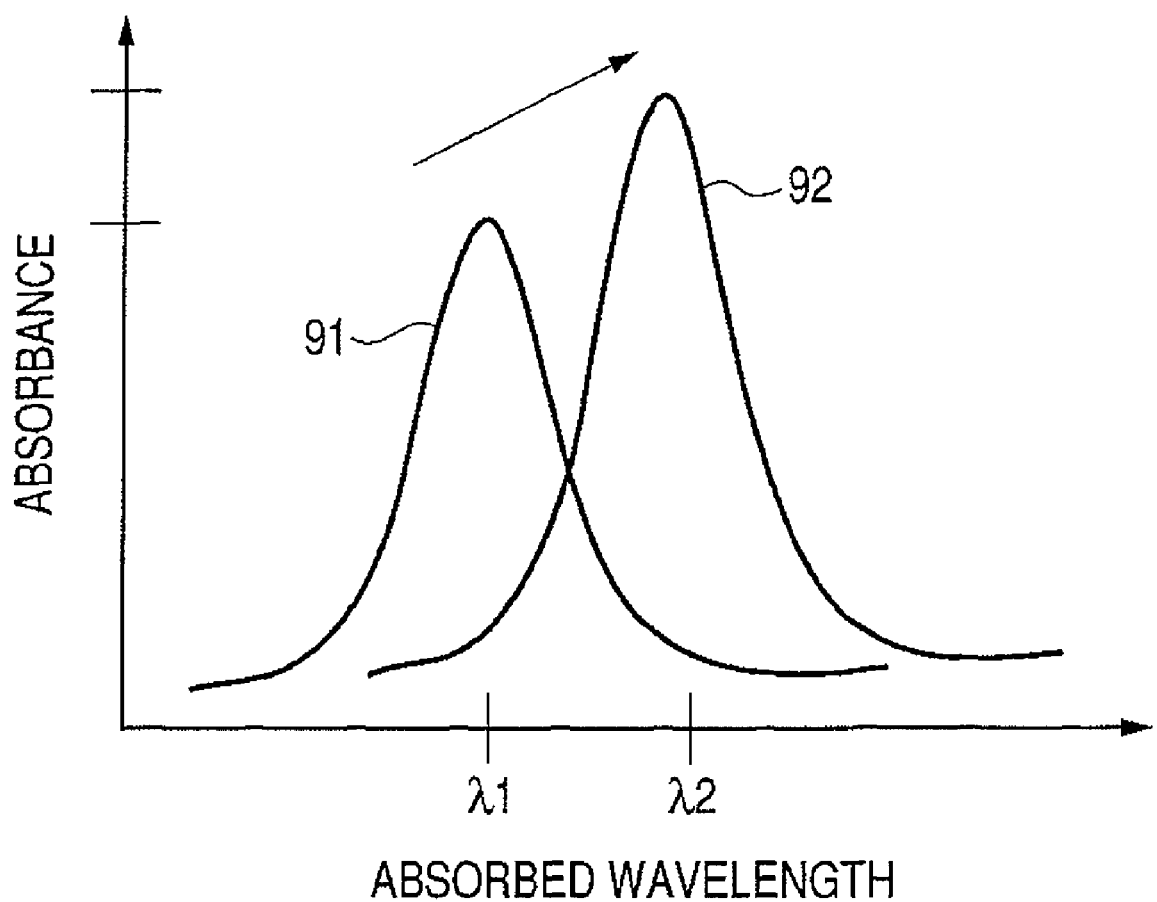
FIG. 9 is a view showing an example of a detected shift of a peak.

When comparing absorption spectra before a reaction and after a reaction as an example shown in FIG. 9, it is understood that the absorption spectrum shifts from a curve 91 to 92 due to a target substance which has been combined with the surface of a detecting element by a specific antigen-antibody reaction. Then, the concentration of a very small amount of AFP in a specimen of which the concentration is unknown can be determined on the basis of a correlation between the concentration of the AFP and the peak intensity of the absorption spectrum or a shifted quantity of a peak wavelength, which has been previously determined by using a known AFP control solution.

It is possible to detect a target substance at sufficient detection sensitivity in a short period of time, by using a detecting element which has been prepared by using a substrate having a metal structure located on a spherical support, according to the preferred embodiment provided by the present invention as described above. In other words, it is possible to effectively disperse the element in a solution by using a spherical support, and to make the element perform a detection reaction in a short period of time. It is also possible to obtain adequate detection sensitivity because the detecting element has a metal structure therein.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-120682, filed Apr. 25, 2006 which is hereby incorporated by reference herein in its entirety.

What is claimed is:

1. A base carrier for detecting a target substance, comprising:
   a support; and
   a plurality of metal structures located on the surface of the support,
   wherein the support is spherical,
   wherein each of the plurality of metal structures has a maximum size within a range of 10 nm to 1450 nm, with the maximum size being defined as the largest distance between an arbitrary set of two points on a respective one of the plurality of metal structures, and
   wherein a distance between adjacent ones of the plurality of metal structures is in a range of 50 nm to 2000 nm.

2. An element for detecting a target substance, comprising:
   a support;
   a plurality of metal structures located on the surface of the support; and
   a capturing body for the target substance located on the plurality of metal structures,
   wherein the support is spherical,
   wherein each of the plurality of metal structures has a maximum size within a range of 10 nm to 1450 nm, with the maximum size being defined as the largest distance between an arbitrary set of two points on a respective one of the plurality of metal structures, and
   wherein a distance between adjacent ones of the plurality of metal structures is in a range of 50 nm to 2000 nm.

3. A detection method for detecting the presence or absence of a target substance in a specimen or detecting a quantity of the target substance, comprising the steps of: making an element for detecting the target substance according to claim 2 contact with a specimen; and detecting a state in which the target substance is captured by the element.

4. A kit for detecting a target substance, comprising: an element for detecting the target substance according to claim 2, and a device for detecting a target substance in a specimen which is comprised of a unit for making the specimen contact with the element and a unit for detecting a capture of the target substance by the element.

* * * * *